(12) United States Patent
Maltz et al.

(10) Patent No.: US 11,311,266 B2
(45) Date of Patent: Apr. 26, 2022

(54) SYSTEMS AND METHODS FOR LIMITED VIEW IMAGING

(71) Applicant: UIH AMERICA, INC., Huston, TX (US)

(72) Inventors: Jonathan Maltz, Huston, TX (US); Supratik Bose, Huston, TX (US)

(73) Assignee: UIH AMERICA, INC., Houston, TX (US)

( * ) Notice: Subject to any disclaimer, the term of this patent is extended or adjusted under 35 U.S.C. 154(b) by 123 days.

(21) Appl. No.: 16/914,551

(22) Filed: Jun. 29, 2020

(65) Prior Publication Data

US 2020/0323510 A1 Oct. 15, 2020

(51) Int. Cl.
| | |
|---|---|
| *A61B 6/00* | (2006.01) |
| *G06T 7/13* | (2017.01) |
| *A61N 5/10* | (2006.01) |
| *A61B 6/03* | (2006.01) |

(52) U.S. Cl.
CPC ............. *A61B 6/541* (2013.01); *A61B 6/032* (2013.01); *A61B 6/5211* (2013.01); *A61N 5/1039* (2013.01); *G06T 7/13* (2017.01); *G06T 2207/10081* (2013.01); *G06T 2207/30004* (2013.01)

(58) Field of Classification Search
CPC ....... A61B 6/541; A61B 6/032; A61B 6/5211; A61B 6/545; A61N 5/1039; A61N 2005/1055; A61N 2005/1062; A61N 5/1067; A61N 5/1049; G06T 7/13; G06T 2207/10081; G06T 2207/30004; G06T 2207/10104; G06T 7/0012; G06T 2207/10088
See application file for complete search history.

(56) References Cited

PUBLICATIONS

Larson et al. "Anisotropic Field-of Views in Radial Imaging" IEEE Transactions on Medical Imaging, vol. 27, No. 1 pp. 47-57 Jan. 2008 (Year: 2008).*
Samuel R. Mazin et al., A Fourier Rebinning Algorithm for Cone Beam CT, Medical Imaging 2008: Physics of Medical Imaging, 2008, 12 pages.
Catherine N. Petchprapa et al., Demystifying Radial Imaging of the Hip, Radiographics, 33(3): 97-112, 2013.

* cited by examiner

*Primary Examiner* — Courtney D Thomas
(74) *Attorney, Agent, or Firm* — Metis IP LLC

(57) ABSTRACT

A system for limited view imaging is provided. The system may obtain a reference image of an object. The system may identify, from the reference image, one or more critical boundaries between a target organ of the object and one or more adjacent organs of the target organ. The system may determine an imaging angle range of the object based on the one or more critical boundaries. The system may further cause an imaging device to scan the object based on the imaging angle range, the object being in a breath-hold state during the scan.

20 Claims, 9 Drawing Sheets

600

---

Determining a plurality of target tangents of the one or more critical boundaries — 610

---

Determining the imaging angle range of the object based on the plurality of target tangents and a scan arc range of the imaging device — 620

# SYSTEMS AND METHODS FOR LIMITED VIEW IMAGING

TECHNICAL FIELD

The present disclosure generally relates to imaging technology, and more particularly, to systems and methods for limited view imaging.

BACKGROUND

Medical imaging is widely used in disease diagnosis and/or treatment. An object (e.g., a patient) may be scanned by an imaging device to acquire image data of the object for analysis. For example, before and/or during a radiotherapy (RT) treatment of a patient (e.g., a cancer patient), one or more imaging devices, such as a computer tomography (CT) device, a magnetic resonance imaging (MRI) device, may be used to perform a scan on a target region (e.g., a tumor) of the patient. A resulting image of the scan may be used to generate or adjust a radiotherapy treatment plan of the patient.

SUMMARY

An aspect of the present disclosure relates to a system for limited view imaging. The system may include at least one storage device including a set of instructions and at least one processor in communication with the at least one storage device. When executing the set of instructions, the at least one processor may be directed to perform operations. The operations may include obtaining a reference image of an object, and identifying, from the reference image, one or more critical boundaries between a target organ of the object and one or more adjacent organs of the target organ. The operations may further include determining an imaging angle range of the object based on the one or more critical boundaries, and causing an imaging device to scan the object based on the imaging angle range, the object being in a breath-hold state during the scan.

In some embodiments, the determining, based on the reference image, one or more critical boundaries between a target organ of the object and one or more adjacent organs of the target organ may include converting the reference image into a binary image; identifying, from the binary image, surfaces of the target organ and the one or more adjacent organs; and determining the one or more critical boundaries which include any tissues to which radiation may be damaging based on a plurality of surface tangents of the surfaces.

In some embodiments, the determining an imaging angle range of the object based on the one or more critical boundaries may include determining a plurality of target tangents of the one or more critical boundaries, and determining the imaging angle range of the object based on the plurality of target tangents and a scan arc range of the imaging device.

In some embodiments, the determining a plurality of target tangents of the one or more critical boundaries may include determining a plurality of candidate tangents of the one or more critical boundaries; for each of the plurality of candidate tangents, determining a weight of the candidate tangent; and selecting, from the plurality of candidate tangents, the plurality of target tangents based on the weights of the plurality of candidate tangents.

In some embodiments, for each of the plurality of candidate tangents, the determining a weight of the candidate tangent may include determining the weight of the candidate tangent based on a dose gradient at a portion of the one or more critical boundaries where the candidate tangent is located.

In some embodiments, for each of the plurality of candidate tangents, the determining a weight of the candidate tangent may include determining the weight of the candidate tangent based on a proximity between the target organ and the one or more adjacent organs at a portion of the one or more critical boundaries where the candidate tangent is located.

In some embodiments, the determining the imaging angle range of the object based on the plurality of target tangents and a scan arc range of the imaging device may include determining a first marginal tangent and a second marginal tangent in the plurality of target tangents; determining whether an angle range between the first marginal tangent and the second marginal tangent is less than the scan arc range; and determining the imaging angle range based on a determination result of whether the angle range between the first marginal tangent and the second marginal tangent is less than the scan arc range.

In some embodiments, the determination result may include that the angle range is less than the scan arc range, and the determining the imaging angle range based on the determination result may include determining the imaging angle range of the object based on the first marginal tangent, the second marginal tangent, and the scan arc range.

In some embodiments, the determination result may include that the angle range exceeds the scan arc range, and the determining the imaging angle range based on the determination result may include dividing, based on the angle range and the scan arc range, the angle range into a first angle range and at least one second angle range, the first angle range being equal to the scan arc range, and for each of the at least one second angle range, determining an equivalent angle range of the second angle range.

In some embodiments, for each of the at least one second angle range, the determining an equivalent angle range of the second angle range may include determining a plurality of candidate angle ranges of the second angle range; for each of the plurality of candidate angle ranges, determining a similarity degree between rays within the candidate angle range and rays within the second angle range; and selecting, among the plurality of candidate angle ranges, the equivalent angle range based on the similarity degrees corresponding to the plurality of candidate angle ranges.

In some embodiments, the operations may further include generating a treatment image based on scan data collected during the scan of the object, and determining a treatment position of the object based on the treatment image and a plan image of the object.

In some embodiments, the operations may further include adjusting a treatment plan of the object based on the treatment image and the plan image of the object.

In some embodiments, the imaging device may be a cone beam computed tomography (CBCT) device.

In some embodiments, the system may include a respiratory sensor configured to detect the breath-hold state of the object during the scan and/or a respiratory controller configured to control the breath-hold state of the object during the scan.

A further aspect of the present disclosure relates to a method for limited view imaging. The method may be implemented on a computing device including at least one processor and at least one storage device. The method may include obtaining a reference image of an object, and identifying, from the reference image, one or more critical boundaries between a target organ of the object and one or more adjacent organs of the target organ. The method may further include determining an imaging angle range of the object based on the one or more critical boundaries, and causing an imaging device to scan the object based on the imaging angle range, the object being in a breath-hold state during the scan.

A still further aspect of the present disclosure relates to a non-transitory computer readable medium including executable instructions. When the executable instructions are executed by at least one processor, the executable instructions may direct the at least one processor to perform a method. The method may include obtaining a reference image of an object, and identifying, from the reference image, one or more critical boundaries between a target organ of the object and one or more adjacent organs of the target organ. The method may further include determining an imaging angle range of the object based on the one or more critical boundaries, and causing an imaging device to scan the object based on the imaging angle range, the object being in a breath-hold state during the scan.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 6 is a flowchart illustrating an exemplary process for determining an imaging angle range of a target organ according to some embodiments of the present disclosure;

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, sections or assembly of different levels in ascending order. However, the terms may be displaced by another expression if they achieve the same purpose.

Figure 2:
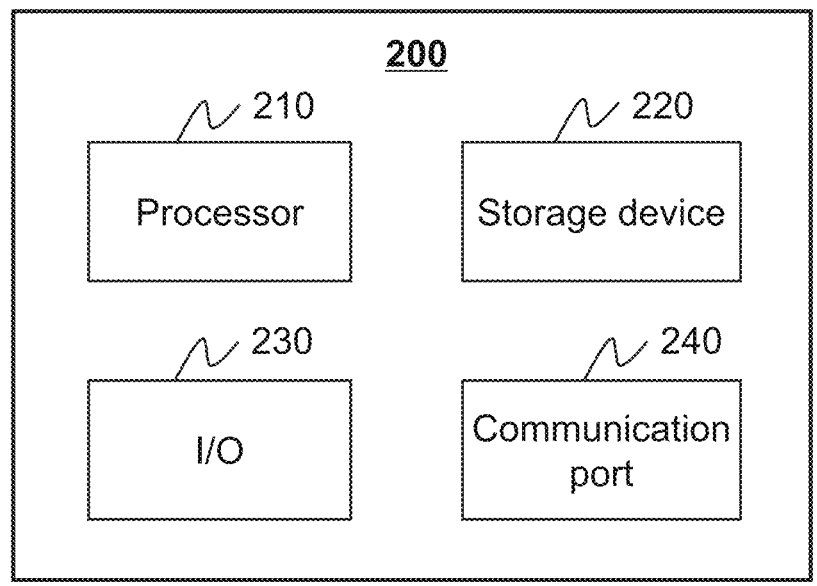
FIG. 2 is a schematic diagram illustrating an exemplary hardware and/or software components of a computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

The term "image" in the present disclosure is used to collectively refer to image data (e.g., scan data, projection data) and/or images of various forms, including a two-dimensional (2D) image, a three-dimensional (3D) image, a four-dimensional (4D) etc. The term "pixel" and "voxel" in the present disclosure are used interchangeably to refer to an element of an image. The term "anatomical structure" in the present disclosure may refer to gas (e.g., air), liquid (e.g., water), solid (e.g., stone), cell, tissue, organ of a subject, or any combination thereof, which may be displayed in an image (e.g., a second image, or a first image, etc.) and really exist in or on the subject's body. The term "region," "location," and "area" in the present disclosure may refer to a location of an anatomical structure shown in the image or an actual location of the anatomical structure existing in or on the subject's body, since the image may indicate the actual location of a certain anatomical structure existing in or on the subject's body.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments of the present disclosure. It is to be expressly understood the operations of the flowcharts may be implemented not in order. Conversely, the operations may be implemented in an inverted order, or simultaneously. Moreover, one or more other operations may be added to the flowcharts. One or more operations may be removed from the flowcharts.

Provided herein are systems and components for non-invasive imaging and/or treatment, such as for disease diagnosis, treatment or research purposes. In some embodiments, the systems may include an RT system, a computed tomography (CT) system, an emission computed tomography (ECT) system, an X-ray photography system, magnetic resonance imaging (MRI) system, or the like, or any combination thereof. For illustration purposes, the disclosure describes systems and methods for radiotherapy.

A medical procedure, e.g., medical imaging, radiation therapy, etc., often involves motion management. For example, a motion management technique may be used in the radiation therapy to ensure that the radiation delivered to a patient (or animal, or another object) matches a planned dose distribution as closely as possible in the presence of motion of a target structure (e.g., a tumor) and/or one or more organs-at-risk (OARs), which include any tissues to which radiation may be damaging. Exemplary motion management techniques used in the radiation therapy may include an image guide radiation therapy (IGRT) technique, a breath-hold technique, or the like, or any combination thereof.

For example, because that the target structure and/or the OAR(s) may change its (or their) position between the time of a planning session and the time of a treatment session, the IGRT technique may be used to adjust the patient position before or during the treatment session to ensure the target structure and/or the OAR(s) is (or are) properly aligned with respect to a delivered treatment field. A treatment plan may need to be adapted to conform to the target structure as presented during the time of the treatment session. During an imaging procedure of the IGRT, the movement of the target structure and/or the OAR(s) may lead to an inconsistency between projections obtained at different angles representing different positions of the target structure and/or the OAR(s), which may affect the quality of a resulting image (e.g., causing a motion artifact in the resulting image).

In order to reduce or eliminate the effect of the movement of the target structure and/or the OAR(s), an imaging component of an RT device may rotate very fast relative to the movement of the target structure and/or the OAR(s). However, the imaging component, such as a CBCT device, typically rotates slowly around the patient relative to the rate of tissue motion, particularly if the imaging component rotates with a gantry of the RT device. For example, a maximum rotation speed of the imaging component may be limited to, for example, 7 degrees per second. It may take 50 seconds for the imaging component to complete a full 360° scan on the patient, during which the patient may take approximately 10 breaths. With each breath, one or more internal organs of the patient may move, which may lead to blurring of the internal regions in the resulting image of the patient. One approach to address this issue caused by the respiratory motion in the imaging procedure of the IGRT is to monitor the respiration motion of the patient during the imaging procedure and divide a respiratory cycle of the patient into a plurality of time bins (or referred to as respiratory phases). Projection data obtained in each of the plurality of time bins may be separately reconstructed to achieve "4-dimensional (4D) CBCT." For example, a 4D CBCT image, which includes a time series of CBCT images, may be reconstructed based on a plurality of sets of projection data obtained in the plurality of time bins. However, an angular increment between successive angles in each reconstruction may be coarse. For example, the patient may take approximately 10 breaths when the imaging components rotates 360°. If the respiratory cycle of the patient is divided into 6 time bins and projection data is obtained at 1 degree interval, the angular interval for each reconstruction in one time bin may be 6 degrees (i.e., a CBCT image corresponding to one time bin may be reconstructed based on projection data acquired in 6 degrees). This may lead to an unacceptable level of image artifact in the 4D-CBCT image.

In order to reduce or eliminate the effect of the respiratory motion of the patient on imaging, the patient is often asked to hold his/her breath during the scan instead of attempting to reconstruct the 4D CBCT image. For example, the patient may be asked to hold his/her breath for a certain period of time, such as 20 seconds, 30 seconds. However, due to a limited breath-holding capability of the patient, or a limited range of projections available on the imaging component, or a need to reduce imaging radiation (e.g., in imaging the contralateral breast in the case of unilateral breast treatment), the imaging of the patient may need to be performed within a limited angle range. A limited angle range refers to a range, the span of which may be smaller than a threshold value, such as 360°. Conventionally, the limited angle range may be an arbitrary angular range, or a default setting of the imaging component, or set manually by a user (e.g., a doctor, a radiologist) of the imaging component. In addition, the same limited angle range may be utilized for scanning different patients and/or different organs of a patient.

To address the above-mentioned problems of conventional limited view imaging techniques, an aspect of the present disclosure provides systems and methods for determining an imaging angle range for limited view imaging. The systems and methods may obtain a reference image (e.g., a CT image, a magnetic resonance [MR] image, a positron emission tomography [PET] image) of an object (e.g., a chest cavity of a patient). According to the reference image, the systems and methods may identify one or more critical boundaries between a target organ (e.g., a pancreas) of the object and one or more adjacent organs (e.g., a duodenum) of the target organ. The systems and methods may determine an imaging angle range of the object based on the one or more critical boundaries. Further, the systems and methods may cause an imaging device (e.g., a CT device, an MRI device) to scan the object based on the imaging angle range. The object may be in a breath-hold state during the scan. A value of performing such a selection of the imaging angle range may be easily illustrated by considering a parallel-ray angular projection of a critical boundary obtained along rays perpendicular to the critical boundary. The parallel-ray angular projection reveals no information regarding the position of the critical boundary or the image intensity change at the critical boundary. However, the parallel-ray angular projection can accurately determine the position of the critical boundary and the image intensity change at the critical boundary. Whether knowledge of the position of the critical boundary is critical to the accurate delivery of treatment, there is benefit in choosing the imaging angle range so as to best discriminate (and in some cases quantify) the critical boundary. During a breath-hold, because the imaging angle range may be limited below that which is considered complete from a tomographic reconstruction perspective, it may be beneficial to select the imaging angle range used that produces the most pertinent information regarding the critical boundary.

According to some embodiments of the present disclosure, the imaging angle range may be determined based on the one or more critical boundaries. For example, a specific weighting scheme may be utilized to optimally determine a plurality of target tangents of the one or more critical boundaries. The imaging angle range may then be selected based on the plurality of target tangents. The determined imaging angle range may preserve adjacent organ(s) of the target organ from unnecessary imaging radiation and/or improve the imaging quality of the object (e.g., by improving the clarity of a critical boundary between the target organ and its adjacent organ(s)). In some embodiments, the scan data collected during the scan of the object may be used to generate a treatment image of the object. The treatment image may be used to guide the implementation of a treatment session of the object. For example, a treatment position of the object may be determined based on the treatment image, and/or a treatment plan of the object may be adjusted based on the treatment image. In the treatment image generated by systems and methods of the present disclosure, the critical boundary between a target and an organ-at-risk (OAR) may have improved clarity and more detailed information, which may improve the accuracy of the treatment positioning and the delivery of the treatment session.

Figure 1:
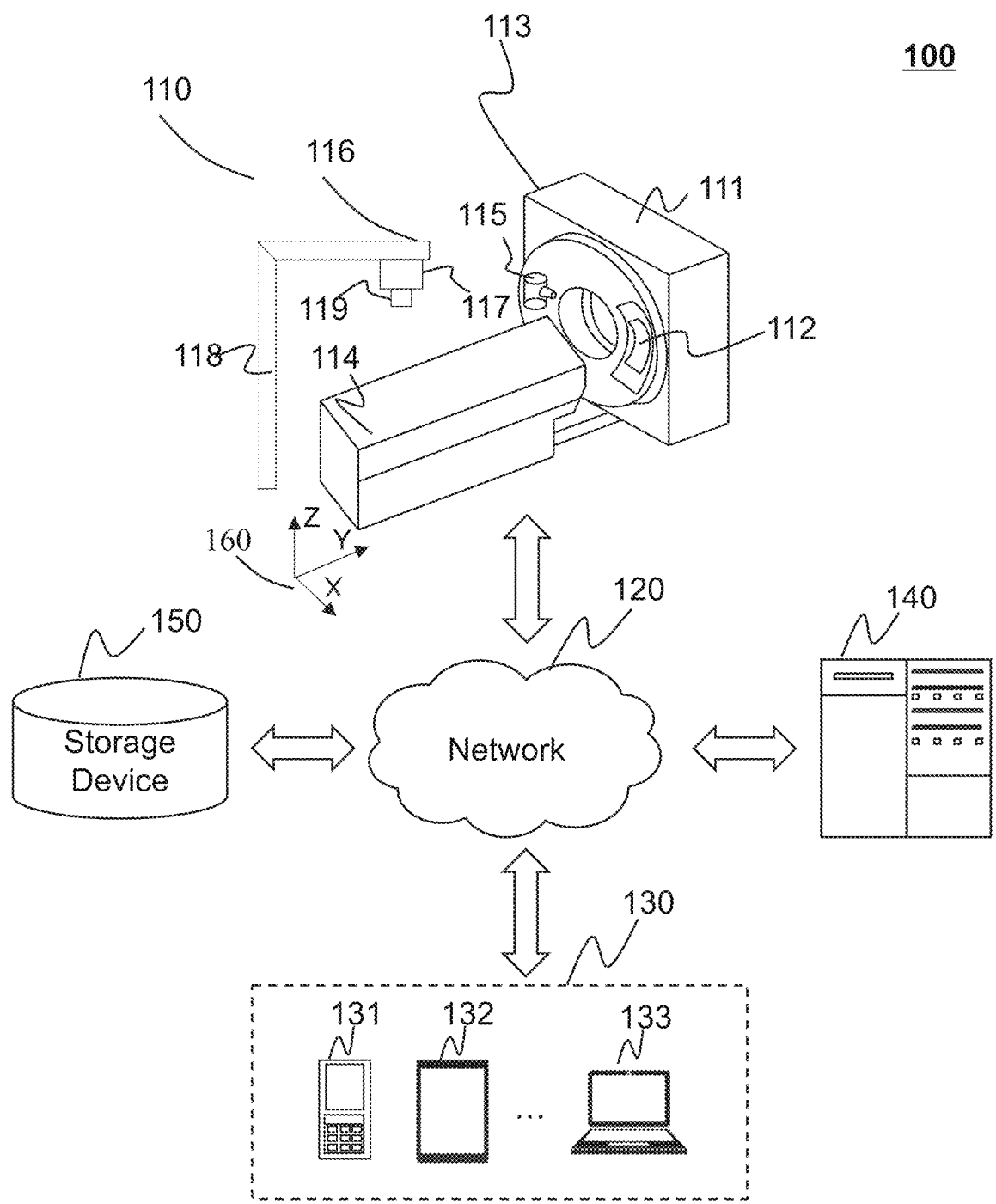
FIG. 1 is a schematic diagram illustrating an exemplary RT system according to some embodiments of the present disclosure.

FIG. 1 is a schematic diagram illustrating an exemplary RT system 100 according to some embodiments of the present disclosure. The RT system 100 may include an RT device 110, a network 120, one or more terminals 130, a processing device 140, and a storage device 150. In some embodiments, two or more components of the RT system 100 may be connected to and/or communicate with each other via a wireless connection (e.g., the network 120), a wired connection, or a combination thereof. The connection between the components of the RT system 100 may be variable. Merely by way of example, the RT device 110 may be connected to the processing device 140 through the network 120 or directly. As a further example, the storage device 150 may be connected to the processing device 140 through the network 120 or directly.

The RT device 110 may be configured to deliver a radiotherapy treatment to an object. For example, the treatment device may deliver one or more radiation beams to a treatment region (e.g., a tumor) of an object for causing an alleviation of the object's symptom. A radiation beam may include a plurality of radiation beamlets. In the present disclosure, "subject" and "object" are used interchangeably. The object may include any biological object (e.g., a human being, an animal, a plant, or a portion thereof) and/or a non-biological object (e.g., a phantom). For example, the object may include a specific portion of a body, such as the head, the thorax, the abdomen, or the like, or a combination thereof, of the object. In some embodiments, the treatment device may be a conformal radiation therapy device, an image-guided radiation therapy (IGRT) device, an intensity-modulated radiation therapy (IMRT) device, an intensity-modulated arc therapy (IMAT) device, an emission guided radiation therapy (EGRT), or the like.

In some embodiments, the RT device 110 may be an IGRT device configured to acquire image data relating to the object and perform a radiotherapy treatment on the object. For example, as illustrated in FIG. 1, the RT device 110 may include an imaging component 113, a treatment component 116, a table (or referred to as couch) 114, or the like. The imaging component 113 may be configured to acquire an image of the object before radiotherapy treatment, during the radiotherapy treatment, and/or after the radiotherapy treatment. In some embodiments, the imaging component 113 may include a computed tomography (CT) device (e.g., a cone beam CT (CBCT) device, a fan beam CT (FBCT) device), a magnetic resonance imaging (MRI) device, an ultrasound imaging device, a fluoroscopy imaging device, a single-photon emission computed tomography (SPECT) device, a positron emission tomography (PET) device, an X-ray imaging device, or the like, or any combination thereof.

In some embodiments, the imaging component 113 may include an imaging radiation source 115, a detector 112, a gantry 111, or the like. The imaging radiation source 115 and the detector 112 may be mounted on the gantry 111. The imaging radiation source 115 may emit radioactive rays to the object. The detector 112 may detect radiation events (e.g., x-ray photons, gamma-ray photons) emitted from the imaging region of the imaging component 113. In some embodiments, the detector 112 may include one or more detector units. The detector unit(s) may include a scintillation detector (e.g., a cesium iodide detector, a gadolinium oxysulfide detector), a gas detector, etc. The detector unit(s) may include a single-row detector and/or a multi-rows detector.

The treatment component 116 may be configured to deliver radiation treatment to the object. The treatment component 116 may include a treatment radiation source 117, a gantry 118, and a collimator 119. The treatment radiation source 117 may be configured to emit treatment radiations towards the object. In some embodiments, the treatment radiation source 117 may include a linear accelerator (LINAC). The collimator 119 may be configured to control the shape of the treatment radiations generated by the treatment radiation source 117.

In some embodiments, the imaging component 113 may be spaced by a distance from the treatment component 116. In some embodiments, rotation axes of the gantry 111 of the imaging component 113 and the gantry 118 of the treatment component 116 may be the same or different. The object may be positioned in different positions on the table 114 for imaging and treatment. In some embodiments, the imaging radiation source 115 and the treatment radiation source 117 may be integrated as one radiation source to image and/or treat the object. In some embodiments, the imaging component 113 and the treatment component 116 may share the same gantry. For example, the treatment radiation source 117 may be mounted on the gantry 111 of the imaging component 113. An object may be placed on the table 114 for treatment and/or imaging.

The couch 114 may be configured to support the object to be treated and/or imaged. In some embodiments, the couch 114 may be movable between the treatment component 116 and the imaging component 113 along a Y-axis direction of a coordinate system 160 as shown in FIG. 1. In some embodiments, the couch 114 may be configured to rotate and/or translate along different directions to move the object to a desired position (e.g., an imaging position under the imaging component 113 for imaging, a treatment position under the treatment component 116 for treatment, etc.).

The network 120 may include any suitable network that can facilitate the exchange of information and/or data for the RT system 100. In some embodiments, one or more components (e.g., the RT device 110, the terminal(s) 130, the processing device 140, the storage device 150, etc.) of the RT system 100 may communicate information and/or data with one or more other components of the RT system 100 via the network 120. For example, the processing device 140 may obtain image data from the RT device 110 via the network 120. As another example, the processing device 140 may obtain user (e.g., a doctor, a radiologist) instructions from the terminal(s) 130 via the network 120. The network 120 may be or include a public network (e.g., the Internet), a private network (e.g., a local area network (LAN)), a wired network, a wireless network (e.g., an 802.11 network, a Wi-Fi network), a frame relay network, a virtual private network (VPN), a satellite network, a telephone network, routers, hubs, switches, server computers, and/or any combination thereof. For example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the RT system 100 may be connected to the network 120 to exchange data and/or information.

Figure 3:
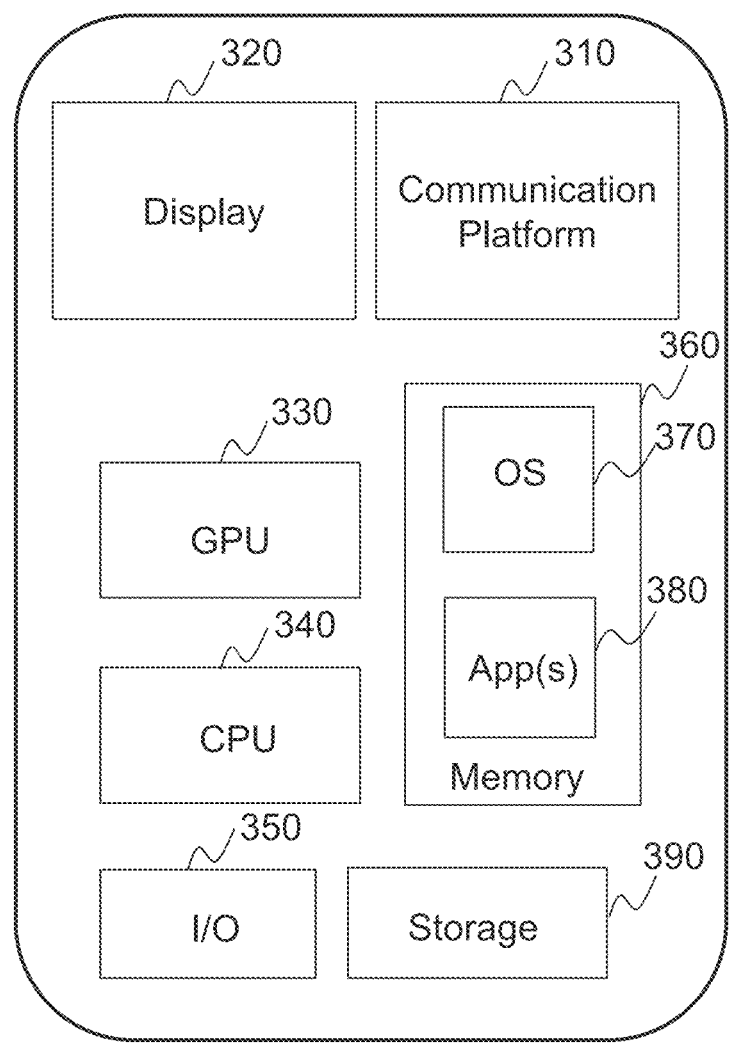
FIG. 3 is a schematic diagram illustrating hardware and/or software components of an exemplary mobile device according to some embodiments of the present disclosure.

The terminal(s) 130 may enable user interaction between a user and the RT system 100. In some embodiments, the terminal(s) 130 may be connected to and/or communicate with the RT device 110, the processing device 140, and/or the storage device 150. For example, the terminal(s) 130 may display a treatment image of the object obtained from the processing device 140. In some embodiments, the terminal(s) 130 may include a mobile device 131, a tablet computer 132, a laptop computer 133, or the like, or any combination thereof. In some embodiments, the mobile device 131 may include a smart home device, a wearable device, a mobile device, a virtual reality device, an augmented reality device, or the like, or any combination thereof. Merely by way of example, the terminal(s) 130 may include a mobile device as illustrated in FIG. 3. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footwear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 130 may be part of the processing device 140.

The processing device 140 may process information obtained from the RT device 110, the terminal(s) 130, and/or the storage device 150. For example, the processing device 140 may obtain a reference image of an object form one or more components (e.g., the RT device 110 (e.g., the imaging component 113), the terminal(s) 130, the storage device 150) of the RT system 100. According to the reference image, the processing device 140 may identify one or more critical boundaries between a target organ of the object and one or more adjacent organs of the target organ. Further, the processing device 140 may determine an imaging angle range of the object based on the one or more critical boundaries and cause an imaging device (e.g., the imaging component 113) to scan the object based on the imaging angle range.

In some embodiments, the processing device 140 may be a single server or a server group. The server group may be centralized or distributed. In some embodiments, the processing device 140 may be local or remote. For example, the processing device 140 may access information stored in the RT device 110, the terminal(s) 130, and/or the storage device 150 via the network 120. As another example, the processing device 140 may be directly connected to the RT device 110, the terminal(s) 130 and/or the storage device 150 to access stored information. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented by a computing device 200 having one or more components as illustrated in FIG. 2.

The storage device 150 may store data, instructions, and/or any other information. In some embodiments, the storage device 150 may store data obtained from the RT device 110, the terminal(s) 130, and/or the processing device 140. For example, the storage device 150 may store the reference image, the scan data, the treatment image, and/or a plan image of the object. In some embodiments, the storage device 150 may store data and/or instructions that the processing device 140 may execute or use to perform exemplary methods described in the present disclosure. In some embodiments, the storage device 150 may include a mass storage device, a removable storage device, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more other components (e.g., the RT device 110, the processing device 140, the terminal(s) 130) of the RT system 100. One or more components of the RT system 100 may access the data and/or instructions stored in the storage device 150 via the network 120. In some embodiments, the storage device 150 may be directly connected to or communicate with one or more other components (e.g., the RT device 110, the processing device 140, the terminal(s) 130) of the RT system 100. In some embodiments, the storage device 150 may be part of the processing device 140.

For illustration purposes, a coordinate system 160 is provided in FIG. 1. The coordinate system 160 may be a Cartesian system including an X-axis, the Y-axis, and a Z-axis. The X-axis and the Y-axis shown in FIG. 1 may be horizontal, and the Z-axis may be vertical. As illustrated, the positive X direction along the X-axis may be from the left side to the right side of the table 114 viewed from the direction facing the front of the RT device 110; the positive Y direction along the Y-axis shown in FIG. 1 may be from the end to the head of the table 114; the positive Z direction along the Z-axis shown in FIG. 1 may be from the lower part to the upper part of the RT device 110.

It should be noted that the above description regarding the RT system 100 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the RT system 100 may include one or more additional components and/or one or more components of the RT system 100 described above may be omitted. For example, the treatment component 116 in the RT device 110 may be omitted. In some embodiments, a component of the RT system 100 may be implemented on two or more sub-components. Two or more components of the RT system 100 may be integrated into a single component. For example, the treatment component 116 in the RT device 110 may be integrated into the imaging component 113.

In some embodiments, limited view imaging methods disclosed herein may be implemented on an imaging system, which may include an imaging device (e.g., a same or similar device as the imaging component 113), the network 120, the storage device 150, the processing device 140, the terminal(s) 130, or the like, or any combination thereof. For illustration purposes, the implementation of the limited view imaging methods on the RT system 100 is described hereinafter, and this is not intended to be limiting.

FIG. 2 is a schematic diagram illustrating exemplary hardware and/or software components of a computing device 200 according to some embodiments of the present disclosure. The computing device 200 may be used to implement any component of the RT system 100 as described herein. For example, the processing device 140 and/or the terminal(s) 130 may be implemented on the computing device 200, respectively, via its hardware, software program, firmware, or a combination thereof. Although only one such computing device is shown, for convenience, the computer functions relating to the RT system 100 as described herein may be implemented in a distributed fashion on a number of similar platforms, to distribute the processing load. As illustrated in FIG. 2, the computing device 200 may include a processor 210, a storage device 220, an input/output (I/O) 230, and a communication port 240.

The processor 210 may execute computer instructions (e.g., program code) and perform functions of the processing device 140 in accordance with techniques described herein. The computer instructions may include, for example, routines, programs, objects, components, data structures, procedures, modules, and functions, which perform particular functions described herein. For example, the processor 210 may process image data obtained from the RT device 110, the terminal(s) 130, the storage device 150, and/or any other component of the RT system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus operations and/or method operations that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage device 220 may store data obtained from one or more components of the RT system 100. In some embodiments, the storage device 220 may include a mass storage device, a removable storage device, a volatile read-and-write memory, a read-only memory (ROM), or the like, or any combination thereof. In some embodiments, the storage device 220 may store one or more programs and/or instructions to perform exemplary methods described in the present disclosure. For example, the storage device 220 may store a program for the processing device 140 to execute to determine an imaging angle range of a target organ of an object. As another example, the storage device 220 may store a program for the processing device 140 to execute to cause an imaging device to scan the object based on the imaging angle range.

The I/O 230 may input and/or output signals, data, information, etc. In some embodiments, the I/O 230 may enable a user interaction with the processing device 140. In some embodiments, the I/O 230 may include an input device and an output device. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to another component (e.g., the processing device 140) via, for example, a bus, for further processing. Other types of the input device may include a cursor control device, such as a mouse, a trackball, or cursor direction keys, etc. The output device may include a display (e.g., a liquid crystal display (LCD), a light-emitting diode (LED)-based display, a flat panel display, a curved screen, a television device, a cathode ray tube (CRT), a touch screen), a speaker, a printer, or the like, or a combination thereof.

The communication port 240 may be connected to a network (e.g., the network 120) to facilitate data communications. The communication port 240 may establish connections between the processing device 140 and the RT device 110, the terminal(s) 130, and/or the storage device 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee™ link, a mobile network link (e.g., 3G, 4G, 5G), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

FIG. 3 is a schematic diagram illustrating exemplary hardware and/or software components of an exemplary mobile device 300 according to some embodiments of the present disclosure. In some embodiments, one or more terminals 130 and/or a processing device 140 may be implemented on a mobile device 300, respectively.

As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™) and one or more applications 380 may be loaded into the memory 360 from the storage 390 in order to be executed by the CPU 340. The applications 380 may include a browser or any other suitable mobile apps for receiving and rendering information relating to the RT system 100. User interactions with the information stream may be achieved via the I/O 350 and provided to the processing device 140 and/or other components of the RT system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4:
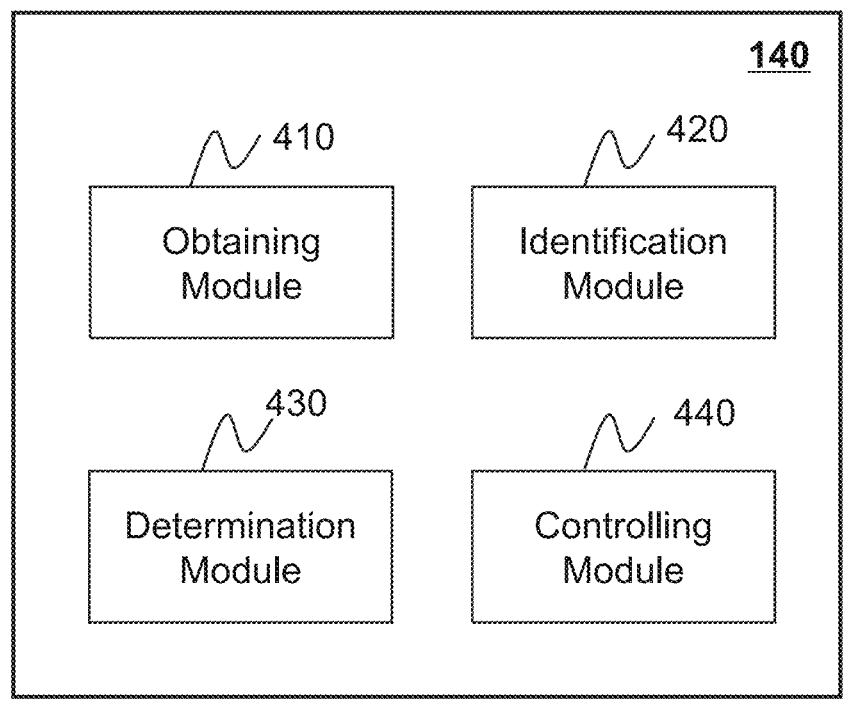
FIG. 4 is a block diagram illustrating an exemplary processing device according to some embodiments of the present disclosure.

FIG. 4 is a block diagram illustrating an exemplary processing device 140 according to some embodiments of the present disclosure. As shown in FIG. 4, the processing device 140 may include an obtaining module 410, an identification module 420, a determination module 430, and a controlling module 440.

The obtaining module 410 may be configured to obtain a reference image of an object. The reference image may include an image of the object, which may be acquired using an imaging device (e.g., the same as or different from the imaging device for scanning the object as described in connection with 540). More descriptions regarding the obtaining of the reference image of the object may be found elsewhere in the present disclosure. See, e.g., operation 510 in FIG. 5 and relevant descriptions thereof.

The identification module 420 may be configured to identify, from the reference image, one or more critical boundaries between the target organ of the object and the one or more adjacent organs of the target organ. Merely by way of example, the identification module 420 may convert the reference image into a binary image in which each pixel (or voxel) has one of two colors, such as black and white. Further, the identification module 420 may identify surfaces of the target organ and the one or more adjacent organs from the binary image. Merely by way of example, the identification module 420 may identify the respective surfaces (e.g., a 2D surface, a 3D surface) of the target organ and the one or more adjacent organs from the binary image, and highlight pixels or voxels corresponding to these surfaces in the binary image. According to a plurality of surface tangents of the surfaces, the identification module 420 may determine the one or more critical boundaries. More descriptions regarding the identification of the one or more critical boundaries may be found elsewhere in the present disclosure. See, e.g., operation 520 in FIG. 5 and relevant descriptions thereof.

The determination module 430 may be configured to determine an imaging angle range of the object based on the one or more critical boundaries. In some embodiments, the determination module 430 may determine a plurality of target tangents of the one or more critical boundaries, and determine the imaging angle range of the object based on the plurality of target tangents of the imaging device. In some embodiments, the determination of the imaging angle range of the object may be based further on a scan arc range of the imaging device. More descriptions regarding the determination of the imaging angle range may be found elsewhere in the present disclosure. See, e.g., operation 530 in FIG. 5, FIG. 6, and relevant descriptions thereof.

The controlling module 440 may be configured to cause the imaging device to scan the object based on the imaging angle range, the object being in a breath-hold state during the scan. In some embodiments, the controlling module 440 may reconstruct a target image (e.g., a CT image or an MR image) based on scan data collected in the scan of the object. The controlling module 440 may generate a treatment image based on scan data collected during the scan of the object. The treatment image may be used to guide the implementation of the treatment session of the object. For example, the controlling module 440 may determine a treatment position of the object based on the treatment image and a plan image of the object. As another example, the controlling module 440 may adjust a treatment plan of the object based on the treatment image and the plan image of the object. More descriptions regarding causing the imaging device to scan the object may be found elsewhere in the present disclosure. See, e.g., operation 540 in FIG. 5 and relevant descriptions thereof.

It should be noted that the above descriptions of the processing device 140 are provided for the purposes of illustration, and not intended to limit the scope of the present disclosure. For persons having ordinary skills in the art, various modifications and changes in the forms and details of the application of the above method and system may occur without departing from the principles of the present disclosure. In some embodiments, the processing device 140 may include one or more other modules and/or one or more modules described above may be omitted. For example, the processing device 140 may also include a transmission module configured to transmit signals (e.g., electrical signals, electromagnetic signals) to one or more components (e.g., the RT device 110, the terminal(s) 130, the storage device 150) of the RT system 100. As a further example, the processing device 140 may include a storage module (not shown) used to store information and/or data (e.g., the reference image, the one or more critical boundaries, the imaging angle range) associated with the limited view imaging. Additionally or alternatively, two or more modules may be integrated into a single module and/or a module may be divided into two or more units. For example, the identification module 420 and the determination module 430 may be combined as a single module which may both identify the one or more critical boundaries and determine the imaging angle range of the object. However, those variations and modifications also fall within the scope of the present disclosure.

Figure 5:
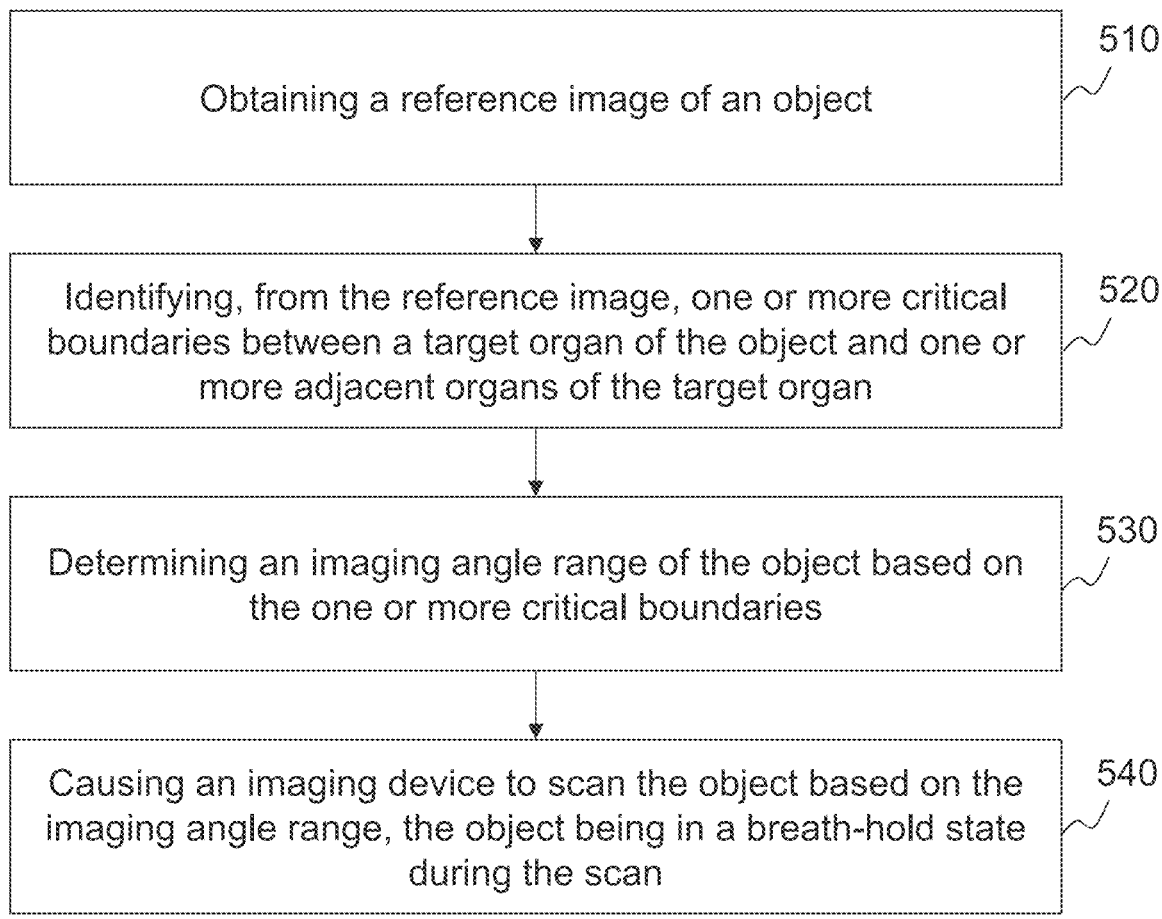
FIG. 5 is a flowchart illustrating an exemplary process for limited view imaging according to some embodiments of the present disclosure.

FIG. 5 is a flowchart illustrating an exemplary process for limited view imaging according to some embodiments of the present disclosure. In some embodiments, process 500 may be executed by the RT system 100. For example, the process 500 may be implemented as a set of instructions (e.g., an application) stored in a storage device (e.g., the storage device 150, the storage device 220, and/or the storage 390). In some embodiments, the processing device 140 (e.g., the processor 210 of the computing device 200, the CPU 340 of the mobile device 300, and/or one or more modules illustrated in FIG. 4) may execute the set of instructions and may accordingly be directed to perform the process 500.

As described elsewhere in this disclosure, during an imaging procedure of an object (e.g., an imaging procedure in an IGRT of the object), one or more organs of the object may move due to a respiratory (or cardiac, or peristaltic, or baseline drift motion) of the object, which may affect the imaging quality of a resulting image of the imaging procedure. In order to eliminate or reduce the effect of the respiratory motion of the object, the object may be asked to hold his/her breath during the scan. In some occasions (e.g., due to a limited breath-holding capability of the object, or a limited range of projections available on an imaging device, or a need to reduce imaging radiation), the imaging procedure of the object may be a limited view imaging procedure. In the limited view imaging procedure, scan data (e.g., projection data) may be obtained in a limited angle range. For example, in a limited view CBCT imaging procedure, a radiation source may rotate in a limited projection angle range (or gantry angle range) smaller than 360° (or smaller than the range needed for half-scan CBCT) to scan (e.g., by emitting radiation toward) the object, or rotate in a full 360° but only scan the object in the limited projection angle range. As another example, in a limited view radial MR imaging procedure (polar scan), angular projection signals (or referred to as radial lines) in a limited projection angle range smaller than 180° may be acquired.

The process 500 may be performed before the scan of the object to determine a suitable angle range for a limited view imaging procedure.

In 510, the processing device 140 (e.g., the obtaining module 410) may obtain a reference image of the object.

The object may include a biological object (e.g., a human, an animal), a non-biological object, or the like, or a combination thereof. For example, the object may include a patient. As another example, the object may include a specific portion, such as the chest, the breast, and/or the abdomen of the patient.

The reference image may include an image of the object, which may be acquired using an imaging device (e.g., the same as or different from the imaging device for scanning the object as described in connection with 540). The object may be in a breathing state or a breath-hold state during the acquisition of the reference image. The reference image may include representations of a target organ of the object and one or more adjacent organs of the target organ. The terms "organ" and "tissue" are used interchangeably referring to a portion of an object. The target organ may include one or more organs that need observation and/or treatment. For example, the target organ may include a region of the object including at least part of malignant tissue (e.g., a tumor, a cancer-ridden organ, or a non-cancerous target of radiation therapy). For example, the target organ may be a tumor, an organ with a tumor, a tissue with a tumor, or any combination thereof, that needs to be treated by radiation. An adjacent organ of the target organ may include an organ in contact with or adjacent to the target organ. Merely by way of example, if a distance between an organ and the target organ is below a threshold distance, the organ may be regarded as an adjacent organ of the target organ. The threshold distance may include a pixel distance in the image domain (e.g., 1 pixel, 2 pixels, 5 pixels, etc.) and/or an actual distance in a physical space (e.g., 0.1 cm, 0.2 cm, 0.3 cm, etc.). The threshold distance may be a default setting of the RT system 100, set manually by a user, or adjusted by processing device 140 according to an actual need.

In some embodiments, the reference image may include a two-dimensional (2D) image, a three-dimensional (3D) image, or the like, or a combination thereof. The reference image may include a CT image (e.g., a cone beam CT (CBCT) image, a fan beam CT (FBCT) image), an MR image, a PET image, an X-ray image, a fluoroscopy image, an ultrasound image, a radiotherapy radiographic image, a SPECT Image, or the like, or a combination thereof.

In some embodiments, the reference image of the object may be previously generated and stored in a storage device (e.g., the storage device 150, the storage device 220, an external storage device). For example, an imaging device (e.g., the imaging component 113 of the RT device 110) may be used to image the object to generate the reference image of the object. Further, the imaging device may transmit the generated reference image to the storage device for storage. The processing device 140 may obtain the reference image from the storage device. In some embodiments, the processing device 140 may cause the imaging device to acquire the reference image by scanning the object and obtain the reference image of the object from the imaging device.

In some embodiments, the limited view imaging procedure of the object may be performed during a radiotherapy treatment (e.g., in a certain treatment session of the object). The reference image may be a plan image (or a portion thereof) generated in a planning stage of the radiation treatment. For example, before the radiotherapy treatment (e.g., days or weeks before the treatment commences) is performed on the object, the plan image of the object may be acquired using an imaging device. The treatment plan may be generated according to the plan image. The processing device 140 may acquire the plan image or a portion of the plan image (e.g., a slice image of the plan image) as the reference image from a storage device storing the plan image.

In 520, the processing device 140 (e.g., the identification module 420) may identify, from the reference image, one or more critical boundaries between the target organ of the object and the one or more adjacent organs of the target organ.

A critical boundary between the target organ and an adjacent organ of the target organ refers to a line in the reference image that separates a representation of the target organ and a representation of the adjacent organ. For example, when the target organ and the adjacent organ of the target organ are in contact with each other, the critical boundary between the target organ and the adjacent organ may be a line that delineates at least a portion of a contact area between the representation of the target organ and the representation of the adjacent organ. As another example, when the target organ and the adjacent organ of the target organ are separated by a certain distance, the critical boundary between the target organ and the adjacent organ may be a line (e.g., a midline) in a gap between the representations of the target organ and the adjacent organ.

In some embodiments, the limited view imaging procedure may be performed during or before a treatment session of the object. The target organ may be the target of the treatment session, such as a tumor. The adjacent organ(s) may include one or more OARs near the target organ. One or more critical boundaries between the target and the OAR(s) may be identified from the reference image. Merely by way of example, the one or more critical boundaries may include a critical boundary between the pancreas and the duodenum, a critical boundary between the prostate and a seminal vesicle, a critical boundary between the prostate and the rectum, a critical boundary between the breast and the heart, a critical boundary between a parotid gland and a nasopharyngeal carcinoma, or the like, or any combination thereof.

In some embodiments, the one or more critical boundaries may be identified manually, semi-automatically, or automatically. In a manual approach, the one or more critical boundaries may be identified from the reference image according to an instruction provided by a user. For example, via a user interface implemented on, e.g., a terminal 130 or a mobile device 300 as illustrated in FIG. 3, a user may mark the one or more critical boundaries in the reference image.

In a semi-automatic approach, the one or more critical boundaries may be identified from the reference image by a computing device (e.g., the computing device 200 as illustrated in FIG. 2) with user intervention. For example, the boundary identification may be performed by the computing device based on an identification algorithm in combination with information provided by a user. Exemplary user intervention in a semi-automatic approach for the boundary identification may include providing a parameter relating to the identification algorithm, providing position parameters relating to the target organ and the one or more adjacent organs of the target organ, making an adjustment to or confirming a preliminary boundary identification performed by the computing device, providing instructions to cause the computing device to repeat or redo the boundary identification, etc.

In an automatic approach, the one or more critical boundaries may be identified from the reference image automatically by a computing device (e.g., the computing device 200 as illustrated in FIG. 2) without user intervention. For example, the one or more critical boundaries may be identified from the reference image automatically by image analysis, for example, according to an image segmentation algorithm, a feature identification algorithm, or the like, or any combination thereof.

Merely by way of example, the processing device 140 may convert the reference image into a binary image in which each pixel (or voxel) has one of two colors, such as black and white. Further, the processing device 140 may identify surfaces of the target organ and the one or more adjacent organs from the binary image. Merely by way of example, the processing device 140 may identify the respective surfaces (e.g., a 2D surface, a 3D surface) of the target organ and the one or more adjacent organs from the binary image, and highlight pixels or voxels corresponding to these surfaces in the binary image. According to a plurality of surface tangents of the surfaces, the processing device 140 may determine the one or more critical boundaries.

For example, for each of the target organ and the one or more adjacent organs of the target organ, the processing device 140 may determine directions of a plurality of surface tangents of the organ. For a specific adjacent organ, the processing device 140 may further determine a critical boundary between the target organ and the specific adjacent organ based on the directions of the surface tangents of the target organ and the directions of the surface tangents of the specific adjacent organ according to a feature identification algorithm. Taking a Hough transform algorithm as an exemplary feature identification algorithm, the processing device 140 may accumulate the directions of the surface tangents of the target organ using a first accumulator. The processing device 140 may accumulate the directions of the surface tangents of the specific adjacent organ using a second accumulator. An accumulator may be a two-dimensional array (or referred to as a cell) used in the Hough transform algorithm to detect the existence of a line. An overlap between the accumulation result generated by the first accumulator and the accumulation result generated by the second accumulator may indicate an orientation of the critical boundary between the target organ and the specific adjacent organ.

In 530, the processing device 140 (e.g., the determination module 430) may determine an imaging angle range of the object based on the one or more critical boundaries.

In some embodiments, the object may be scanned by an imaging device according to the imaging angle range (which will be described in detail in connection with operation 540). The imaging angle range of the object refers to a scanning angle range of the imaging device in which scan data is acquired during the scan (i.e., operation 540) to be performed on the object. More descriptions regarding the imaging angle range may be found elsewhere in the present disclosure. See, e.g., operation 540 and relevant descriptions thereof.

In some embodiments, the processing device 140 may determine a plurality of target tangents of the one or more critical boundaries, and determine the imaging angle range of the object based on the plurality of target tangents of the imaging device. In some embodiments, the determination of the imaging angle range of the object may be based further on a scan arc range of the imaging device. More descriptions regarding the determination of the imaging angle range may be found elsewhere in the present disclosure. See, e.g., FIG. 7 and relevant descriptions thereof.

In 540, the processing device 140 (e.g., the controlling module 440) may cause the imaging device to scan the object based on the imaging angle range, the object being in a breath-hold state during the scan.

In some embodiments, the object may remain in the breath-hold state during the whole scan. Alternatively, the object may be in a breath-hold state during a portion of the scanning and a breathing state during the remaining portion of the scan. For example, the object may take a plurality of breath-holds and be allowed to breathe for a period between successive breath-holds of the plurality of breath-holds. The imaging device may be, for example, a CT device, an MRI device, or another imaging device as described elsewhere in this disclosure (e.g., FIG. 1 and the relevant descriptions).

For example, a CBCT scan or a tomosynthesis scan may be performed on the object to acquire projection data of the object in a plurality of first projection angles, such as a plurality of projection images in the first projection angles. The range of the first projection angles may be referred to as the imaging angle range of the object during the CBCT scan or the tomosynthesis scan. By scanning the object within the imaging angle range determined based on the one or more critical boundaries, the target organ may be scanned and the adjacent organs of the target organ may be preserved from unnecessary imaging radiation. In addition, the imaging angle range may be selected based on data analysis, rather than arbitrarily or manually determined, which may improve the imaging quality of the scan performed on the object, for example, improving the clarity of a critical boundary between the target organ and its adjacent organ. Merely by way of example, for a short CBCT scan in which views are acquired over an arc of a minimum of 180 degrees plus the cone angle, compared with reducing imaging angle range, the selection of the imaging angle range may increase a spatial sampling of a critical boundary between the target organ and its adjacent organ that is located away from an imaging isocenter and may lead to better visualization of the critical boundary. Specifically, the selection of the imaging angle range may increase sampling frequency (i.e., reduce sampling interval angle) of the critical boundary between the target organ and its adjacent organ, which may improve spatial resolution of the critical boundary. As another example, a limited angle CBCT scan (e.g., tomosynthesis) usually uses a limited imaging angle to visualize a critical boundary (e.g., a critical boundary including high-frequency information). The limited imaging angle may be selected to best resolve the critical boundary by performing methods as described in connection with operation 530.

As another example, the imaging device may be an MRI device, and an MR scan (e.g., a radial MR scan) may be performed by the MRI device on the object according to the imaging angle range. During a radial MR scan (or referred to as a polar MR scan), a gradient field may be controlled to obtain angular projection signals (or referred to as radial lines) at a plurality of second projection angles. The angular projection signals may be analogous to the projection images (e.g., parallel beam x-ray projection images) acquired in the CBCT scan or the tomosynthesis scan as aforementioned. The angular projection signals may be used to fill a Fourier space (i.e., a k-space), and an inverse Fourier transform may be performed on the angular projection signals to reconstruct an MR image of the object. The range of the second projection angles may be referred to as the imaging angle range of the object during the radial MR scan. In some embodiments, the object may hold his/her breath during the radial MR scan. During the breath-hold radial MR scan, the acquisition of each projection may take time, so a limited count of angular projection signals may be obtained. The systems and methods according to embodiments of the present disclosure may be used to select the second projection angles of the angular projection signals (i.e., the imaging angle range of the radial MR scan), so that an improved radial sampling of k-space may be achieved in order to clearly visualize the one or more critical boundaries in the resulting MR image. For example, the second projection angles may be aligned with the one or more critical boundaries. Additionally or alternatively, one or more second projection angles parallel to best sampling tangents of the one or more critical boundaries (e.g., a plurality of target tangents as described in connection with FIG. 7) may be obtained first. Merely by way of example, the radial MRI scan may be used to enhance one or more critical boundaries in an image of the hip of a patient. In some embodiments, the MR scan may be an intrafractional MR scan that is performed during treatment. For example, the intrafractional MR may be performed using, e.g., MRIDIAN by VIEWRAY, UNITY by ELEKTA.

In some embodiments, the processing device 140 may reconstruct a target image (e.g., a CT image or an MR image) based on scan data collected in the scan of the object. In some embodiments, the scan may be performed on the object before (e.g., minutes or hours before) a treatment session starts or during the treatment session. The processing device 140 may generate a treatment image based on scan data collected during the scan of the object. The treatment image may be used to guide the implementation of the treatment session of the object. For example, the processing device 140 may determine a treatment position of the object based on the treatment image and a plan image of the object. The treatment position refers to a position for the object to receive the treatment session. As another example, the processing device 140 may adjust a treatment plan of the object based on the treatment image and the plan image of the object.

Conventionally, before (e.g., days or weeks before) the radiotherapy treatment commences, a plan image (e.g., a CT image) of the object may be acquired using an imaging device (e.g., the same imaging device as the one for acquiring the treatment image or another imaging device). As used herein, the plan image refers to an image acquired at a treatment planning stage. In some embodiments, a treatment plan for the object may be made according to the plan image. The treatment plan may describe how the radiotherapy treatment is planned to be performed on the object. The treatment plan may include information including, e.g., how one or more beams are delivered to the target organ of the object during each treatment session over the course of treatment lasting a certain period of time, e.g., days. For example, the treatment plan may provide a total dose (e.g., 0.1 Gy, 10 Gy, 50 Gy, 100 Gy, etc.) and a dose distribution in the target organ. In some embodiments, the plan image may be acquired by a limited angle imaging at the time of planning. The angle range of the limited angle imaging may be a default setting of the RT system 100, or set manually by a user (e.g., a doctor, a radiologist), or determined based on the process 500 described in the present disclosure. Alternatively, the plan image may be acquired by a full angle imaging (e.g., a 360° scan) at the time of planning.

The treatment plan may be delivered to the object during several treatment sessions, spread over a treatment period of multiple days (e.g., 2 to 5 weeks). However, during the treatment period, setup errors may occur, and an anatomical change (e.g., weight loss; growth, shrinkage, or disappearance of a tumor; the appearance of a new tumor, etc.) may take place within the object. The size and/or position of a certain organ may change between the time of planning and the time of a treatment session. Therefore, every time the object comes for a specific treatment session, to ensure accurate positioning of the object for the execution of the specific treatment session, the object may be scanned for generating the treatment image. The anatomical change of the object may be identified by comparing (e.g., registering) the plan image and the treatment image. In some embodiments, the plan image may be acquired by limited angle imaging at the time of planning. The treatment image may be compared with the original plan image. Alternatively, the plan image may be acquired by a full angle imaging at the time of planning. The processing device 140 may generate a synthesized limited angle image based on the plan image, and compare the treatment image with the synthesized limited angle image.

In some embodiments, the treatment position of the object in a current treatment session may then be determined based on the comparison result between the plan image and the treatment image. Additionally or alternatively, if the comparison result indicates a visible or non-negligible anatomical change (e.g., a disappearance of a tumor, the appearance of a new tumor, the size of a tumor changes for more than a threshold value) within the object, the treatment plan of the object may be adjusted based on the comparison result between the plan image and the treatment image. More descriptions regarding the treatment image may be found elsewhere in the present disclosure. See, e.g., FIG. 9 and relevant descriptions thereof.

In some embodiments, the system may include a respiratory sensor and/or a respiratory controller. Merely by way of example, the respiratory sensor may include a belt, a respiratory inductive plethysmograph, a passive or active optical system, a millimeter wave system, a radar system, a spirometer, an imaging system, etc. The respiratory sensor may be configured to control the breath-hold state of the object during the scan. For example, when projection data from different imaging angle ranges are combined, it is understood that the breath-hold state is appreciably similar. This may be verified via the respiratory sensor. In some embodiments, the respiratory sensor may be guided by an audio or visual feedback system. Merely by way of example, the respiratory controller may include a mechanical respiration system (e.g., an Elekta Active Breathing Coordinator). The respiratory sensor may be configured to detect the breath-hold state of the object during the scan.

It should be noted that the above description regarding the process 500 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 500 may be accomplished with one or more additional operations not described and/or without one or more of the operations discussed above. For example, the process 500 may include an additional transmitting operation to transmit the generated treatment image to a terminal device (e.g., a terminal 130 of a doctor) for display. As another example, the process 500 may include an additional storing operation to store information and/or data (e.g., the reference image, the one or more critical boundaries, the imaging angle range) associated with the limited view imaging in a storage device (e.g., the storage device 150) disclosed elsewhere in the present disclosure.

FIG. 6 is a flowchart illustrating an exemplary process 600 for determining an imaging angle range of a target organ according to some embodiments of the present disclosure. In some embodiments, process 600 may be executed by the RT system 100. For example, the process 600 may be implemented as a set of instructions (e.g., an application) stored in a storage device (e.g., the storage device 150, the storage device 220, and/or the storage 390). In some embodiments, the processing device 140 (e.g., the processor 210 of the computing device 200, the CPU 340 of the mobile device 300, and/or one or more modules illustrated in FIG. 4) may execute the set of instructions and may accordingly be directed to perform the process 600. In some embodiments, one or more operations of the process 600 may be performed to achieve at least part of operation 530 as described in connection with FIG. 5.

In 610, the processing device 140 (e.g., the determination module 430) may determine a plurality of target tangents of the one or more critical boundaries.

There is an infinite number of tangents of the one or more critical boundaries. A target tangent of a critical boundary refers to a tangent of the one or more critical boundaries that is selected from tangents of the one or more critical boundaries for determining the imaging angle range. In some embodiments, a target tangent of the one or more critical boundaries may have a higher weight (which indicates its importance) than other tangents of the one or more critical boundaries. The weight of a tangent may be set manually by a user or adjusted by processing device 140 according to an actual need or a default setting of the RT system 100.

Merely by way of example, a tangent may be with respect to a specific portion of the one or more critical boundaries. For example, the tangent may be a tangent of a point on a critical boundary between the target organ and a specific adjacent organ of the target organ. The weight of the tangent with respect to a portion of a critical boundary may be determined based on a proximity between the target organ and the one or more adjacent organs at the portion of the one or more critical boundaries. The proximity between the target organ and the specific adjacent organ may be measured by, for example, the shortest distance (e.g., a pixel distance in the image domain or a real distance in the physical world) between the target organ and the specific adjacent organ. In some embodiments, the higher the proximity, the higher the weight of the tangent. For instance, a tangent of the critical boundary between the target organ and the specific adjacent organ that are close to each other (high proximity) may be assigned with a higher weight than a tangent of the critical boundary between the target organ and the specific adjacent organ that are far away from each other (low proximity). As another example, a tangent of the critical boundary between the target organ and a specific adjacent organ whose distance from each other is below a threshold (high proximity) may be assigned with a higher weight than a tangent of the critical boundary between the target organ and a specific adjacent organ whose distance from each other exceeds a threshold (low proximity). In some embodiments, the weights of tangents of the critical boundary (or boundaries) between the target organ and specific adjacent organ(s) may be different for different promiximities between the target organ and the specific adjacent organ(s). In some embodiments, the promiximities between the target organ and specific adjacent organ(s) may be divided into groups, and the weights of tangents of the critical boundary (or boundaries) between the target organ and specific adjacent organ(s) may be assigned based on their respective proximity groups. In some embodiments, the weights of tangents of the critical boundary (or boundaries) between the target organ and specific adjacent organ(s) may be the same for those in a same proximity group.

Additionally or alternatively, the weight of the tangent with respect to a portion of a critical boundary may be determined based on a dose gradient at the portion of the critical boundary. A dose gradient at the specific portion may indicate a difference between the radiation dose at the specific portion and the radiation dose at a position near the specific portion (e.g., a position in a certain distance to the specific portion) in a specified direction. The dose gradient may be determined at a treatment planning stage, for example, defined in a treatment plan of the object. In some embodiments, the higher the dose gradient at the specific portion, the higher the weight of the tangent. For instance, a tangent located at a high dose gradient region (e.g., a critical boundary between a target and an OAR) may be assigned with a higher weight than a tangent located at a low dose gradient region (e.g., a critical boundary between two OARs). Merely by way of example, if the target organ is the pancreas (a target), the specific adjacent organ is the duodenum (an OAR), the dose gradient of a critical boundary between the pancreas and the duodenum may be high (e.g., higher than a threshold gradient). A tangent of the critical boundary between the pancreas and the duodenum may be more heavily weighted. As another example, a tangent located at region where a dose gradient exceeds a threshold may be assigned with a higher weight than a tangent located at a region where a dose gradient is below a threshold. In some embodiments, the weights of tangents at different regions may be different for different dose gradients at the different regions. In some embodiments, the weight of the tangent may be determined based on the direction of the dose gradient at the specific portion where the tangent is located.

In some embodiments, the processing device 140 may determine a plurality of candidate tangents of the one or more critical boundaries. For example, the processing device 140 may determine a certain count of candidate tangents of the one or more critical boundaries. The processing device 140 may further select the target tangents from the candidate tangents. For example, the processing device 140 may randomly select the plurality of target tangents from the plurality of candidate tangents. In some embodiments, the weights are determined for the target tangents.

In some embodiments, for each of the plurality of candidate tangents, the processing device 140 may determine a weight of the candidate tangent. The weight of a candidate tangent with respect to a portion of a critical boundary may be determined based on a dose gradient at the portion of the critical boundary and/or proximity between the target organ and the one or more adjacent organs at the portion. Further, the processing device 140 may select the plurality of target tangents based on the weights of the plurality of candidate tangents from the plurality of candidate tangents. For example, the processing device 140 may select two or more candidate tangents with a weight larger than a threshold weight from the plurality of candidate tangents as the plurality of target tangents. The threshold weight may be a default setting of the RT system 100, set manually by a user, or adjusted by processing device 140 according to an actual need or a default setting of the RT system 100. As another example, the processing device 140 may select candidate tangents with the highest N weights from the plurality of candidate tangents as the plurality of target tangents. N may be any positive integer greater than 1.

By selecting the target tangents, the imaging angle range determined based on the target tangents may be more accurate, which may improve the imaging quality of the generated target image. For example, the target tangents may be determined based on the proximity between the target organ and the one or more adjacent organs so that a critical boundary between adjacent organs may have higher clarity and/or more detailed information in the target image acquired based on a scanning in the imaging angle range. As another example, the target tangents may be determined based on the dose gradient so that in the target image, details of a region having a high dose gradient may be presented more clearly, specifically in the direction of the dose gradient.

In 620, the processing device 140 (e.g., the determination module 430) may determine the imaging angle range of the object based on the plurality of target tangents and a scan arc range of the imaging device.

As used herein, a scan arc range of an imaging device refers to a maximum scanning angle range of the imaging device available during a scan of the object (e.g., a scan as described in connection with operation 540). In some embodiments, the scan arc range may be previously determined and stored in a storage device (e.g., the storage device 150, the storage device 220, an external storage device). For example, before the object is scanned, a user (e.g., a doctor or a radiologist) may manually determine the scan arc range by analyzing the condition (e.g., a position of a diseased organ, a breathing ability) of the object. Further, the user may input the scan arc range into the storage device via a user interface implemented on, e.g., a terminal 130 or a mobile device 300 as illustrated in FIG. 3. The processing device 140 may obtain the scan arc range from the storage device.

Alternatively, the processing device 140 may automatically determine the scan arc range based on one or more parameters of the imaging device and/or the condition of the object. For example, the imaging device may be capable of scanning the object in a limited projection range due to limited equipment conditions, and the scan arc range may be the limited projection range. As another example, the processing device 140 may determine the scan arc range based on a determination of whether imaging radiation applied to the object during the imaging needs to be reduced. If the imaging radiation needs to be reduced (e.g., one or more critical organs, such as the contralateral breast, may need to be protected from imaging radiation), the processing device 140 may determine the scan arc range based on, for example, positions of the one or more critical organs. As a further example, the processing device 140 may determine the scan arc range based on a rotation speed of the imaging device and the breath-hold capability (e.g., a breath-holding time) of the object. Merely by way of example, the processing device 140 may determine a product (e.g., 7°/s*20 s=140°) of the rotation speed (e.g., 7°/s) of the imaging device and the breath-holding time (e.g., 20 s) of the object as the scan arc range (e.g., 140°) of the imaging device.

Figure 7:
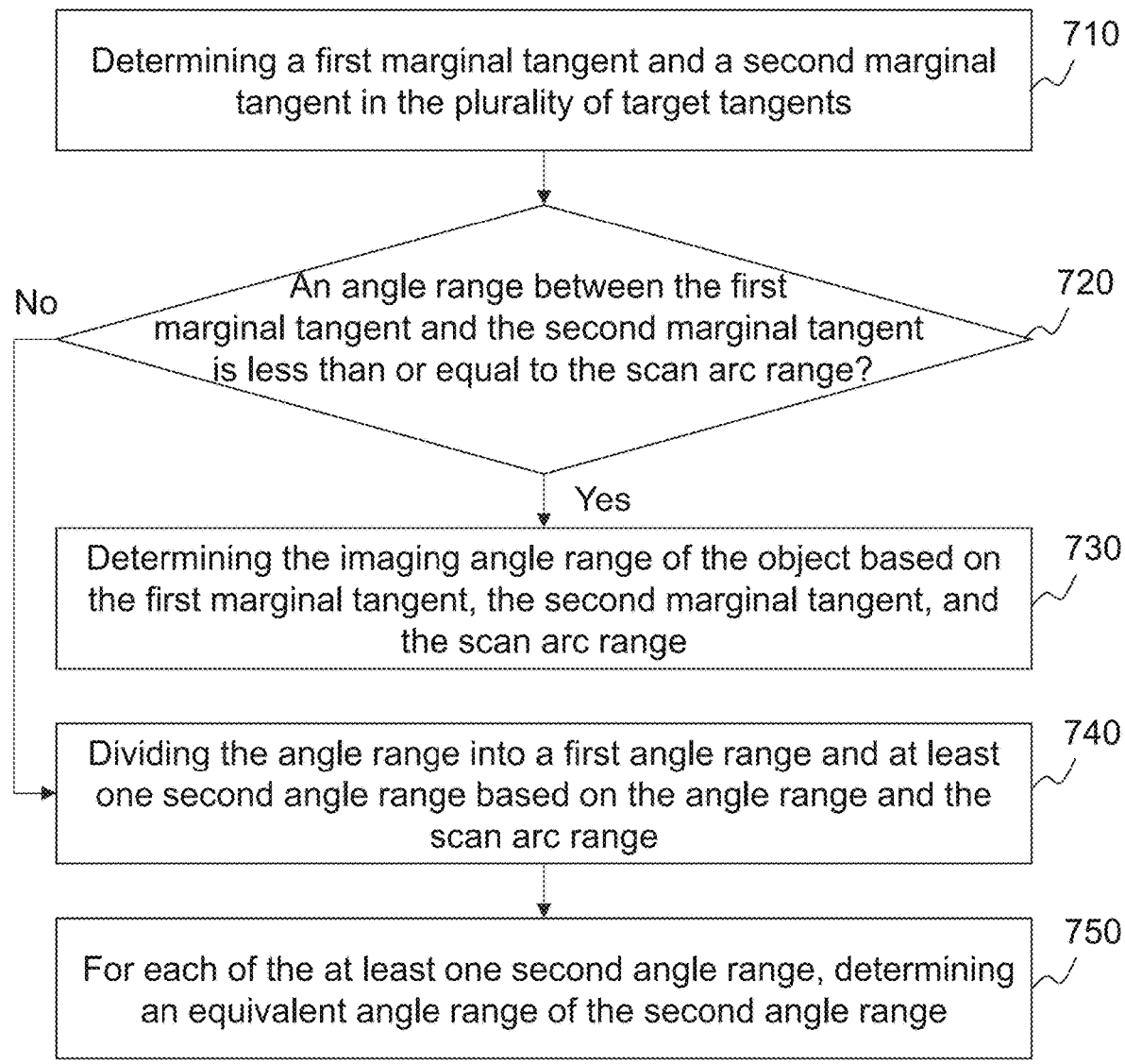
FIG. 7 is a flowchart illustrating an exemplary process for determining an imaging angle range of a target organ according to some embodiments of the present disclosure.

After the scan arc range of the imaging device is obtained or determined, the processing device 140 may determine the imaging angle range of the object based on the target tangents and the scan arc range of the imaging device. In some embodiments, the processing device 140 may perform one or more operations of process 700 as shown in FIG. 7 to determine the imaging angle range of the object based on the target tangents and the scan arc range of the imaging device.

In 710, the processing device 140 (e.g., the determination module 430) may determine a first marginal tangent and a second marginal tangent in the plurality of target tangents. The first marginal tangent and the second marginal tangent may be a pair of target tangents, an angle between which is the greatest among all possible pairs of target tangents of the plurality of target tangents.

In some embodiments, the processing device 140 may determine an angle between each of the plurality of target tangents and a reference direction, and determine the first marginal tangent and the second marginal tangent based on the angles of the target tangents. The reference direction may be any direction. Merely by way of example, the processing device 140 may determine an angle of 0° in the vertical direction of the reference image as the reference direction. As another example, the processing device 140 may determine a direction perpendicular to a coronal plane of the object as the reference direction. For each of the plurality of target tangents, the processing device 140 may determine an angle between the target tangent and the vertical direction. The processing device 140 may designate a target tangent with the smallest angle with respect to the vertical direction, among the determined target tangents, as the first marginal tangent and a target tangent with the largest angle with respect to the vertical direction, among the determined target tangents, as the second marginal tangent, or designate the target tangent with the largest angle as the first marginal tangent and the target tangent with the smallest angle as the second marginal tangent. More descriptions regarding the determination of the first and second marginal tangents may be found elsewhere in the present disclosure. See, e.g., FIG. 8 and relevant descriptions thereof.

In 720, the processing device 140 (e.g., the determination module 430) may determine whether an angle range between the first marginal tangent and the second marginal tangent is below the scan arc range. According to a determination result of whether the angle range between the first marginal tangent and the second marginal tangent is below the scan arc range, the processing device 140 may determine the imaging angle range of the object.

For example, the determination result may include that the angle range between the first marginal tangent and the second marginal tangent is below the scan arc range. When the angle range is below the scan arc range, the process 700 may proceed to operation 730. In 730, the processing device 140 (e.g., the determination module 430) may determine the imaging angle range of the object based on the first marginal tangent, the second marginal tangent, and the scan arc range. For example, the processing device 140 may determine a middle line between the first marginal tangent and the second marginal tangent based on the angle of the first marginal tangent with respect to the reference direction and the angle of the second marginal tangent with respect to the reference direction. According to the middle line and the scan arc range, the processing device 140 may determine a start angle and an end angle of the imaging angle range. More descriptions regarding the determination of the imaging angle range when the angle range is below the scan arc range may be found elsewhere in the present disclosure. See, e.g., FIG. 8 and relevant descriptions thereof.

As another example, the determination result may include that the angle range between the first marginal tangent and the second marginal tangent exceeds the scan arc range. When the angle range exceeds the scan arc range, the process 700 may proceed to operations 740 and 750. In 740, the processing device 140 (e.g., the determination module 430) may divide the angle range into a first angle range and at least one second angle range based on the angle range between the first and second marginal tangents and the scan arc range. The first angle range may be equal to the scan arc range. For example, assuming that the angle range is 40° to 70° and the scan arc range is 40° to 60°, the processing device 140 may divide the angle range 40° to 70° into a first angle range 40° to 60° (which is equal to the scan arc range) and a second angle range 60° to 70°. As aforementioned, in some embodiments, the scan arc range may be determined based on a breath-hold capability of the object. During the scan, the object may be able to hold his/her breath in the first angle range (i.e., the scan arc range) and need to breathe after the first angle range.

In 750, for each of the at least one second angle range, the processing device 140 may determine an equivalent angle range of the second angle range.

As used herein, if a specific angle range can be used to acquire substantially the same scan data of the object as or similar scan data of the object to a second angle range, the specific angle range may be regarded as an equivalent angle range of the second angle range. Merely by way of example, in X-ray imaging, a first scan in an angle range A and a second scan in an angle range (180°+A) may be used to scan the object in opposite views and acquire substantially the same or similar scan data of the object. The angle range (180°+A) may be regarded as an equivalent angle range of the angle range A.

In some embodiments, for a second angle range, the processing device 140 may determine an opposite angle range by adding 180° to the second angle range and designate the opposite angle range as the equivalent angle range of the second angle range. For example, the equivalent angle range of a second angle range 60° to 70° may be equal to 240° to 250°. In some embodiments, the processing device 140 may determine a plurality of candidate angle ranges of the second angle range, and select the equivalent angle range from the plurality of candidate angle ranges. Merely by way of example, the processing device 140 may determine the opposite angle range of the second angle range. Then, the processing device 140 may designate the opposite angle range and/or one or more angle ranges close to the opposite angle range as the plurality of candidate angle ranges of the second angle range. For example, candidate angle ranges of a second angle range 60° to 70° may include 240° to 250°, 241° to 251°, 239° to 249°, 240° to 252°, 238° to 250°, or the like, or any combination thereof. In some embodiments, the candidate angle ranges may be set manually by a user or adjusted by processing device 140 according to an actual need or a default setting of the RT system 100.

The equivalent angle range may be selected from the plurality of candidate angle ranges randomly, manually, or according to a certain selection rule. Merely by way of example, for each of the plurality of candidate angle ranges, the processing device 140 may determine a similarity degree between first rays within the candidate angle range and second rays within the second angle range. The similarity degree between the first rays within a candidate angle range and the second rays within the second angle range may indicate a similarity degree between the candidate angle range and the second angle range. The higher the similarity degree between the first rays within a candidate angle range and the second rays within the second angle range, the higher the similarity degree between the candidate angle range and the second angle range. For example, the processing device 140 may simulate a plurality of first rays within a candidate angle range and a plurality of second rays within the second angle range based on a system geometry of the imaging device (e.g., a distance between a radiation source and a detector of the imaging device). Each of the second rays may correspond to one of the first rays, and a corresponding pair of second ray and first ray may have the same orientation or similar orientations. In some embodiments, the processing device 140 may map similarly orientated rays in a candidate angle range and the second angle range using a rebinning algorithm, e.g., a Fourier-rebinning algorithm. For example, cone beam rays may be rebinned to parallel rays according to a Fourier rebinning algorithm for CBCT. Similar orientated rays of the parallel rays may be determined by converting the parallel rays using an inverse operation of the Fourier rebinning algorithm. More descriptions regarding the Fourier rebinning algorithm may be found in, for example, a paper entitled "A Fourier Rebinning Algorithm for Cone Beam CT," published in *Medical Imaging* 2008: *Physics of Medical Imaging,* 6913:691323, the contents of which are hereby incorporated by reference.

The processing device 140 may determine a dot product between each corresponding pair of first ray and second ray. The processing device 140 may further determine the similarity degree between the first rays and the second rays based on a sum of the dot products of the plurality of pairs of first ray and second ray. A dot product between two rays refers to a dot product between vectors representing the two rays. The higher the sum of the dot products, the higher the similarity degree between the first and second rays. In some embodiments, the processing device 140 may determine the similarity degree between the first and second rays using one or more other similarity algorithms, such as a Pearson correlation coefficient, a Euclidean distance similarity, a cosine similarity, a Hausdorff distance, etc.

Further, for a second angle range, the processing device 140 may select, among the plurality of candidate angle, the equivalent angle range of the second angle range ranges based on the similarity degrees corresponding to the plurality of candidate angle ranges. For example, the processing device 140 may select a candidate angle range with the largest similarity degree as the equivalent angle range of the second angle range. The processing device 140 may further designate the first angle range and the equivalent angle range corresponding to each second angle range as the imaging angle range of the object.

In some embodiments, a limited view imaging may be performed by an imaging device on the object according to the imaging angle range of the object. Taking a CBCT scan of the object as an example, a gantry of the imaging device may rotate around the object during the scan, a radiation source of the imaging device may emit X-rays toward the object when the gantry angle of the gantry is within the first angle range and the equivalent angle range(s) of the at least one second angle range. For example, the first angle range may be 40° to 60° and the equivalent angle range(s) may be 240° to 250°. The radiation source may emit X-rays when the gantry angle is in the range of 40° to 60°, stop emitting X-rays when the gantry angle is in the range of 60° to 240°, and resume emitting X-rays when the gantry angle is in the range of 240° to 250°. The object may be asked to hold his/her breath when the gantry angle is in the range of 40° to 60° and again in the range of 240° to 250°, and take a breath when the gantry angle is in the range of 60° to 240°. Scan data (or projection data) collected in the limited view imaging may be reconstructed into a target image of the object. By selecting the equivalent angle range of each second angle range according to a similarity metric as aforementioned, the imaging angle range of the object may be determined in a more precise manner, which may improve the visualization (e.g., the clarity) of the one or more critical boundaries between the target organ and the adjacent organ(s) of the target organ.

It should be noted that the above description regarding the process 600 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 8:
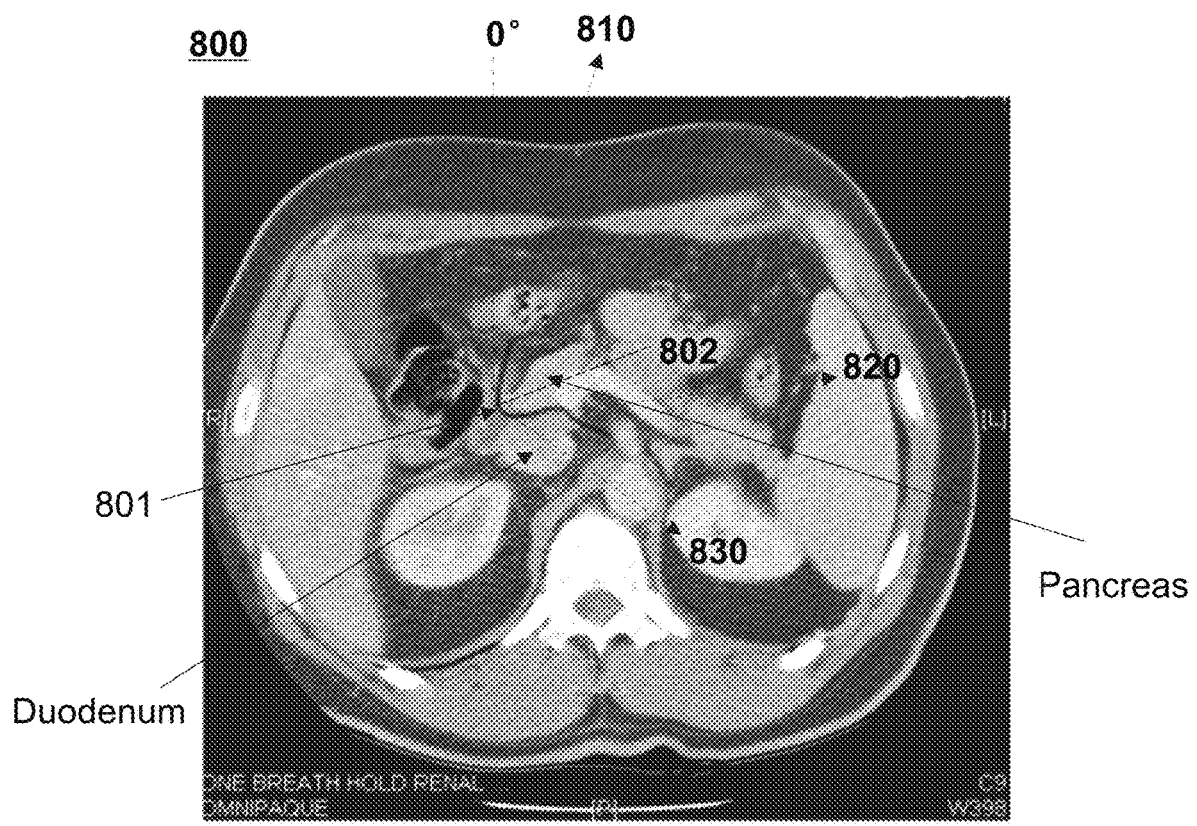
FIG. 8 is a schematic diagram illustrating an exemplary reference image of the chest cavity of a patient according to some embodiments of the present disclosure.

FIG. 8 is a schematic diagram illustrating an exemplary reference image 800 of the chest cavity of a patient according to some embodiments of the present disclosure. The reference image 800 is a CT image illustrating a cross-section of the chest cavity of the patient. For example, the target organ may be the pancreas in the chest cavity and an adjacent organ of the target organ may be the duodenum, a critical boundary 801 between the pancreas and the duodenum may be determined as shown in FIG. 8.

For illustration purposes, an exemplary process of determining an imaging angle range for the patient based on the reference image 800 is described hereinafter. As illustrated in FIG. 8, the processing device 140 may determine a plurality of target tangents 810, 820, and 830 of the critical boundary 801, for example, by performing operation 610 as described in connection with FIG. 6. The processing device 140 may determine a first marginal tangent and a second marginal tangent among the target tangents. The angle between the target tangents 810 and 830 may be higher than an angle between the target tangents 810 and 820 and an angle between the target tangents 820 and 830. Accordingly, the target tangents 810 and 830 may be designated as the first marginal tangent and the second marginal tangent, respectively. The angle between the target tangent 810 and a reference direction 0° illustrated in FIG. 8 may be 20.5°, the angle between the target tangent 820 and the reference direction may be 87.4°, and the angle between the target tangent 830 and the reference direction may be 130.7°. By comparing the angles of the target tangents 810, 820, and 830, the target tangent 810 with the minimum angle of 20.5° may be determined as the first marginal tangent and the target tangent 830 with the maximum angle of 130.7° may be determined as the second marginal tangent.

Assuming that a scan arc range of the imaging device used to image the chest cavity of the patient is 140°, an angle range)(130.7°−20.5°=110.2° between the first marginal tangent 810 and the second marginal tangent 830 is less than the scan arc range. The processing device 140 may determine a middle line 802 between the first marginal tangent 810 and the second marginal tangent 830, wherein an angle of the middle line with respect to the reference direction may be equal to)(20.5°+130.7°/2, i.e., 75.6°. Further, the processing device 140 may determine that a start angle of the imaging angle range is equal to (75.6°−140°/2) (i.e., 5.6°), and an end angle of the imaging angle range is equal to (75.6°+140°/2))(i.e., 145.6°. The imaging angle range of the object is 5.6° to 145.6°.

Figure 9A:
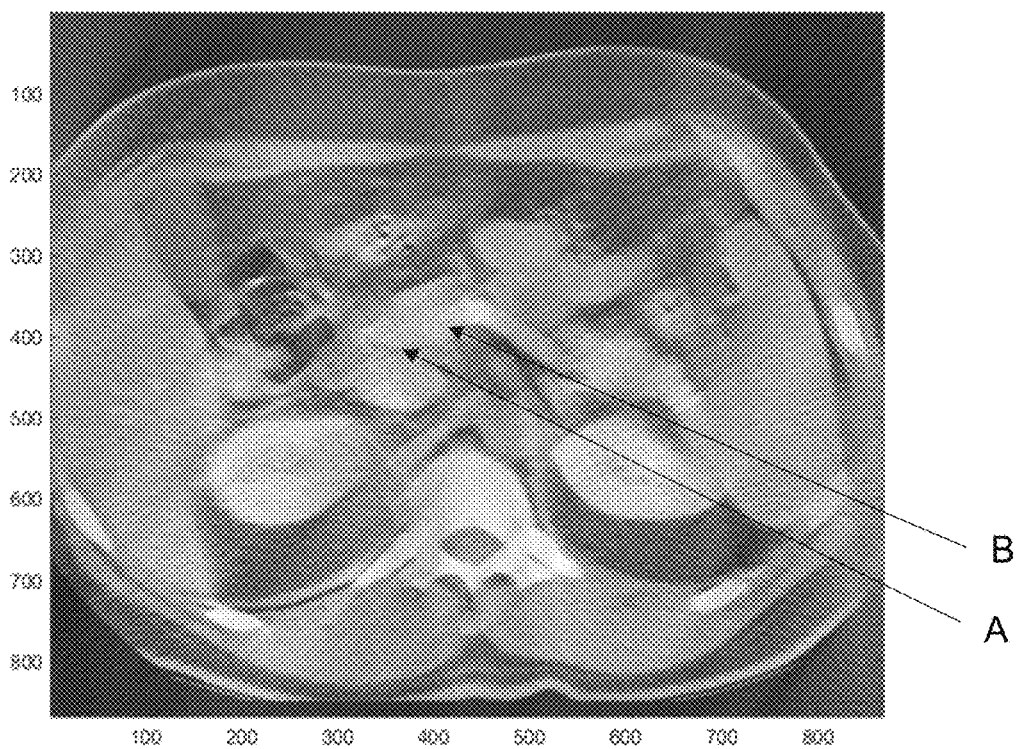
FIGS. 9A and 9B are schematic diagrams illustrating exemplary target images of the chest cavity of a patient according to some embodiments of the present disclosure.
Figure 9B:
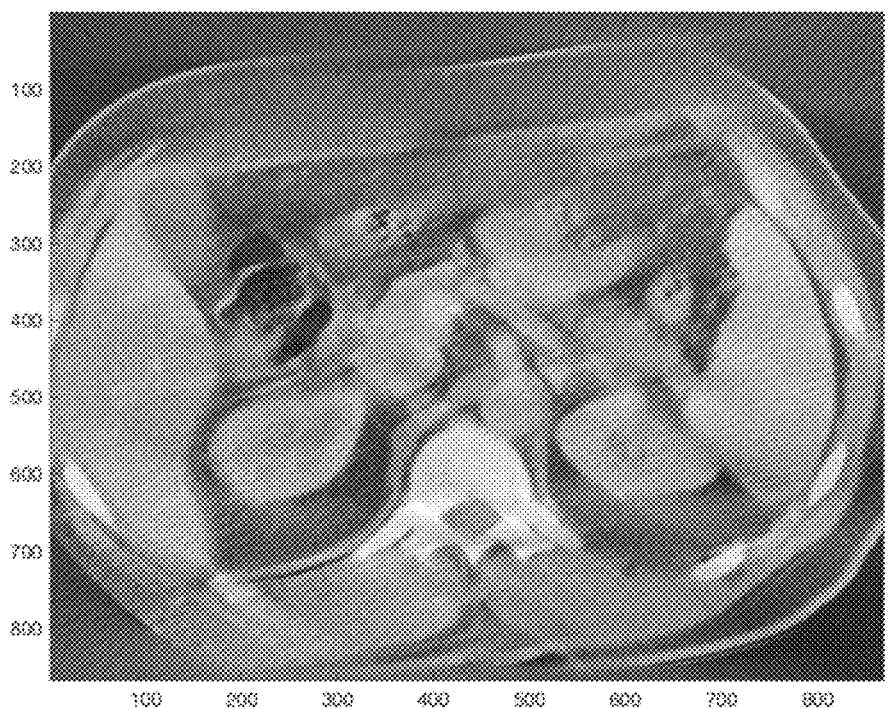

FIGS. 9A and 9B are schematic diagrams illustrating exemplary target images of the chest cavity of a patient according to some embodiments of the present disclosure. A target image 900A as illustrated in FIG. 9A was generated based on scan data collected during a first scan of the chest cavity. The first scan was performed in an imaging angle range 5.6° to 145.6°, which was determined by performing the process of determining an imaging angle range as described in connection with FIG. 8. A target image 900B as illustrated in FIG. 9B was generated based on scan data collected during a second scan of the chest cavity. The second scan was performed in an imaging angle range 95.6° to 234.6°, which was selected randomly. Compared with the target image 900B, the target image 900A has a higher image quality. For example, the boundary (as indicated by A) between the pancreas and the duodenum is clearer in the target image 900A. In addition, the target image 900A includes more details (as indicated by B) than the target image 900B. It suggests that the systems and methods disclosed herein for determining an imaging angle range may improve the imaging quality of the patient.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claimed subject matter may lie in less than all features of a single foregoing disclosed embodiment.

We claim:

1. A system for limited view imaging, comprising:
at least one storage device including a set of instructions; and
at least one processor in communication with the at least one storage device, wherein when executing the set of instructions, the at least one processor is directed to perform operations including:
obtaining a reference image of an object;
identifying, from the reference image, one or more critical boundaries between a target organ of the object and one or more adjacent organs of the target organ;
determining an imaging angle range of the object based on the one or more critical boundaries; and
causing an imaging device to scan the object based on the imaging angle range, the object being in a breath-hold state during the scan.

2. The system of claim 1, wherein the determining, based on the reference image, one or more critical boundaries between a target organ of the object and one or more adjacent organs of the target organ comprises:
converting the reference image into a binary image;
identifying, from the binary image, surfaces of the target organ and the one or more adjacent organs; and
determining the one or more critical boundaries which include any tissues to which radiation may be damaging based on a plurality of surface tangents of the surfaces.

3. The system of claim 1, wherein the determining an imaging angle range of the object based on the one or more critical boundaries comprises:
determining a plurality of target tangents of the one or more critical boundaries; and
determining the imaging angle range of the object based on the plurality of target tangents and a scan arc range of the imaging device.

4. The system of claim 3, wherein the determining a plurality of target tangents of the one or more critical boundaries comprises:
determining a plurality of candidate tangents of the one or more critical boundaries;
for each of the plurality of candidate tangents, determining a weight of the candidate tangent; and
selecting, from the plurality of candidate tangents, the plurality of target tangents based on the weights of the plurality of candidate tangents.

5. The system of claim 4, wherein for each of the plurality of candidate tangents, the determining a weight of the candidate tangent comprises:
determining the weight of the candidate tangent based on a dose gradient at a portion of the one or more critical boundaries where the candidate tangent is located.

6. The system of claim 4, wherein for each of the plurality of candidate tangents, the determining a weight of the candidate tangent comprises:
determining the weight of the candidate tangent based on a proximity between the target organ and the one or more adjacent organs at a portion of the one or more critical boundaries where the candidate tangent is located.

7. The system of claim 3, wherein the determining the imaging angle range of the object based on the plurality of target tangents and a scan arc range of the imaging device comprises:
determining a first marginal tangent and a second marginal tangent in the plurality of target tangents;
determining whether an angle range between the first marginal tangent and the second marginal tangent is less than the scan arc range; and
determining the imaging angle range based on a determination result of whether the angle range between the first marginal tangent and the second marginal tangent is less than the scan arc range.

8. The system of claim 7, wherein
the determination result includes that the angle range is less than the scan arc range; and
the determining the imaging angle range based on the determination result includes determining the imaging angle range of the object based on the first marginal tangent, the second marginal tangent, and the scan arc range.

9. The system of claim 7, wherein:
the determination result includes that the angle range exceeds the scan arc range; and
the determining the imaging angle range based on the determination result comprises:
dividing, based on the angle range and the scan arc range, the angle range into a first angle range and at least one second angle range, the first angle range being equal to the scan arc range; and
for each of the at least one second angle range, determining an equivalent angle range of the second angle range.

10. The system of claim 9, wherein for each of the at least one second angle range, the determining an equivalent angle range of the second angle range comprises:
determining a plurality of candidate angle ranges of the second angle range;
for each of the plurality of candidate angle ranges, determining a similarity degree between rays within the candidate angle range and rays within the second angle range; and
selecting, among the plurality of candidate angle ranges, the equivalent angle range based on the similarity degrees corresponding to the plurality of candidate angle ranges.

11. The system of claim 1, wherein the at least one processor is directed to perform the operations further comprising:
generating a treatment image based on scan data collected during the scan of the object; and
determining a treatment position of the object based on the treatment image and a plan image of the object.

12. The system of claim 11, wherein the at least one processor is directed to perform the operations further comprising:

adjusting a treatment plan of the object based on the treatment image and the plan image of the object.

13. The system of claim 1, wherein the imaging device is a cone beam computed tomography (CBCT) device.

14. The system of claim 1, wherein the system includes at least one of a respiratory sensor configured to detect the breath-hold state of the object during the scan and a respiratory controller configured to control the breath-hold state of the object during the scan.

15. A method for limited view imaging, the method being implemented on a computing device including at least one processor and at least one storage device, the method comprising:
obtaining a reference image of an object;
identifying, from the reference image, one or more critical boundaries between a target organ of the object and one or more adjacent organs of the target organ;
determining an imaging angle range of the object based on the one or more critical boundaries; and
causing an imaging device to scan the object based on the imaging angle range, the object being in a breath-hold state during the scan.

16. The method of claim 15, wherein the determining an imaging angle range of the object based on the one or more critical boundaries comprises:
determining a plurality of target tangents of the one or more critical boundaries; and
determining the imaging angle range of the object based on the plurality of target tangents and a scan arc range of the imaging device.

17. The method of claim 16, wherein the determining the imaging angle range of the object based on the plurality of target tangents and a scan arc range of the imaging device comprises:
determining a first marginal tangent and a second marginal tangent in the plurality of target tangents;
determining whether an angle range between the first marginal tangent and the second marginal tangent is less than the scan arc range; and
determining the imaging angle range based on a determination result of whether the angle range between the first marginal tangent and the second marginal tangent is less than the scan arc range.

18. The method of claim 17, wherein
the determination result includes that the angle range is less than the scan arc range; and
the determining the imaging angle range based on the determination result includes determining the imaging angle range of the object based on the first marginal tangent, the second marginal tangent, and the scan arc range.

19. The method of claim 17, wherein:
the determination result includes that the angle range exceeds the scan arc range; and
the determining the imaging angle range based on the determination result comprises:
dividing, based on the angle range and the scan arc range, the angle range into a first angle range and at least one second angle range, the first angle range being equal to the scan arc range; and
for each of the at least one second angle range, determining an equivalent angle range of the second angle range.

20. A non-transitory computer readable medium, comprising executable instructions that, when executed by at least one processor, direct the at least one processor to perform a method, the method comprising:
obtaining a reference image of an object;
identifying, from the reference image, one or more critical boundaries between a target organ of the object and one or more adjacent organs of the target organ;
determining an imaging angle range of the object based on the one or more critical boundaries; and
causing an imaging device to scan the object based on the imaging angle range, the object being in a breath-hold state during the scan.

* * * * *